United States Patent [19]

Gallegra et al.

[11] Patent Number: 5,292,949
[45] Date of Patent: Mar. 8, 1994

[54] PROCESS FOR THE PREPARATION OF ACID ANHYDRIDES

[75] Inventors: Pasquale Gallegra, Muttenz; Gerhard Degischer, Füllinsdorf, both of Switzerland

[73] Assignee: Saurefabrik Schweizerhall, Schweizerhalle, Switzerland

[21] Appl. No.: 991,407

[22] Filed: Dec. 16, 1992

[30] Foreign Application Priority Data

Dec. 20, 1991 [CH] Switzerland .................... 3813/91

[51] Int. Cl.$^5$ .................... C07C 51/567; C07C 53/18
[52] U.S. Cl. .................................................... 562/897
[58] Field of Search ........................... 562/897, 894

[56] References Cited

U.S. PATENT DOCUMENTS

| | | | |
|---|---|---|---|
| 4,024,129 | 5/1977 | Henniger et al. | 562/897 X |
| 4,117,008 | 9/1978 | Klenk et al. | 260/545 R |
| 4,175,188 | 11/1979 | Klenk et al. | 544/182 |
| 4,238,412 | 12/1980 | Findeisen et al. | 260/545 R |
| 4,284,584 | 8/1991 | Findeisen | 260/545 R |
| 4,309,538 | 1/1982 | Schmidt et al. | 544/182 |
| 4,315,094 | 2/1982 | Bonse et al. | 564/182 |
| 4,328,340 | 5/1982 | Bonse et al. | 544/182 |
| 4,345,100 | 8/1982 | Bonse et al. | 564/124 |
| 4,456,565 | 6/1984 | Findeisen et al. | 260/545 R |
| 4,470,932 | 9/1984 | Findeisen | 260/546 |
| 4,595,541 | 1/1981 | Amiet et al. | 260/546 |
| 4,874,558 | 10/1989 | Fife et al. | 262/894 |

FOREIGN PATENT DOCUMENTS

| | | |
|---|---|---|
| 0029176 | 5/1981 | European Pat. Off. . |
| 0168293 | 1/1986 | European Pat. Off. . |
| 2224161 | 11/1973 | Fed. Rep. of Germany . |
| 2642140 | 3/1978 | Fed. Rep. of Germany . |
| 3037301 | 6/1982 | Fed. Rep. of Germany . |
| 3144791 | 5/1983 | Fed. Rep. of Germany . |

OTHER PUBLICATIONS

Manfred et al., Chemical Abstracts, vol. 97 (1982), Abstract No. 127286f.

Bayer AG, Derwent Abstracts 46090 E/23 (1973).

Draber et al., Chemical Abstracts, vol. 80 (1974), p. 369, Abstract No. 48042u.

Deutsche Gold und Silber, Chemical Abstracts, vol. 88 (1978) p. 725 Abstract No. 190425e.

(List continued on next page.)

*Primary Examiner*—Arthur C. Prescott
*Attorney, Agent, or Firm*—Wenderoth, Lind & Ponack

[57] ABSTRACT

The invention relates to a novel process for the preparation of symmetrical acid anhydrides of general formula

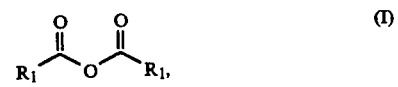

(I)

which process comprises reacting a compound of formula

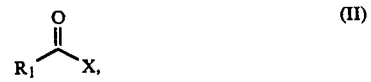

(II)

with an acid anhydride of formula

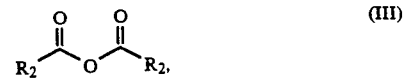

(III)

with removal by distillation of the compound of formula

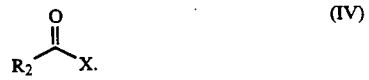

(IV)

$R_2$ and X are as defined in the description, and X is chloro or bromo.

24 Claims, No Drawings

OTHER PUBLICATIONS

Pielartzik et al., Houben-Weyl, Methoden der Organischen Chemie, vol. E5. pp. 633–653 (1979).

Youngs et al., J. Am. Oil Chemiste Socl., vol. 35, pp. 416–417 (1958).

Leiderer, Derwent Abstracts 04410S-AE Abstracting DT-1932303 published Jan. 14, 1971.

Adduchi et al., Org. Prep. Proc., vol. 2, No. 4, pp. 321–329 (1970).

Davidson et al., J. Am. Chem. Soc., 1952, pp. 1515–1516.

Gerard et al., J. Chem. Soc., 1952, pp. 741–742.

Gerard et al., J. Chem. Soc., 1953, pp. 2117–2120.

Edwards, J. Chem. Soc. (C), 1966, pp. 1734–1737.

Diago–Miseguer et al., Synthesis, 1980, pp. 547–551.

Zielinski et al., Syntahesis, 1976, pp. 185–187.

Cremlyn et al., J. C. S. Perkin I, 1972, pp. 583–586.

Mestres et al., Synthesis, 1981, pp. 218–220.

Mestres et al., Synthesis, 1982, pp. 288–291.

Cabre-Castellvi et al., Synthesis, 1981, pp. 616–622.

Hasselmann, Chem. Abstracts, vol. 55, 25760b Abstracting German 1 100 612 published Mar. 2, 1961.

Brewster et al., J. Am. Chem. Soc., vol. 77, pp. 6214–6215 (1955).

Kostyuk et al., J. Appl. Chem. USSR, vol. 35, pp. 679–680 (1962).

Kuhn et al., Monatshefte für Chemie, vol. 97, No. 5, pp. 1534–1540 (1966).

Rothstein et al., J. Chem. Soc., 1965, pp. 4566–4575.

Gutsche et al., J. Am. Chem. Soc., vol. 80, pp. 3711–1714 (1958).

Hajicek et al., Coll. Czechoslovak Chem. Commun., vol. 46, pp. 1262–1271 (1981).

Rinderknecht et al., Organic Syntheses, vol. 47, John Wiley & Sons (1967) pp. 89–92.

Albertson, Organic Reactions, vol. 12, John Wiley & Sons, Inc. 1962 pp. 157–355.

Nelson et al., J. Org. Chem., vol. 28, pp. 1905–1907 (1963).

Allen et al., Organic Syntheses, vol. 3, Harning et al., (eds) John Wiley & Sons, Inc., 1955, pp. 28–30.

Leiderer, Chem. Abstr. vol. 74 (1971) p. 431 Abstract No. 125208h Abstracting Ger. Offen. 1932303 Jan. 14, 1971.

Smalley et al., J. Chem. Soc., 1964, pp. 755–756.

PROCESS FOR THE PREPARATION OF ACID ANHYDRIDES

The present invention relates to a novel process for the preparation of specific carboxylic acid derivatives, namely symmetrical anhyrides.

Methods of preparing symmetrical carboxylic acid anhydrides are described, inter alia, in Houben-Weyl, "Methoden der Organischen Chemie" (Methods of Organic Chemistry), Supplementary Volume and Sequel to the 4th Edition Vol. E5 "Carbonsäuren und Carbonsäure-Derivate" (Carboxylic acids and Derivatives), Stuttgart/New York 1985, pp. 633 to 652.

There is a need for economical methods for synthesising symmetrical carboxylic acid anhydrides, important objects being in particular a simple reaction mechanism and working up. Especially desirable are those methods that permit the final product to be obtained in increased yield and that allow good and simple isolation thereof.

Specifically, the invention relates to a novel process for the preparation of symmetrical acid anhydrides of general formula

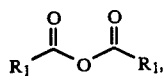
(I)

wherein $R_1$ is an aliphatic, cycloaliphatic, aromatic, cycloaliphatic-aliphatic or araliphatic radical, with the proviso that functional groups present in $R_1$, if necessary, are in protected form, which process comprises reacting a compound of formula

(II)

wherein $R_1$ has the meanings assigned to it above, and wherein X is chloro or bromo, with an acid anhydride of formula

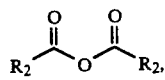
(III)

wherein $R_2$ is an aliphatic hydrocarbon radical or cycloalkyl, with removal by distillation of the compound of formula

(IV)

wherein $R_2$ and X have the meanings assigned to them above, and removing any protective groups present.

The novel process makes it possible to prepare the corresponding symmetrical acid anhydrides from acid chlorides by reaction with acid anhydrides of different structure in very high yield and purity. The acid chlorides or bromides of formula IV, which are useful in organic synthesis, are formed in the reaction as by-products.

The novel simplified process for the preparation of symmetrical carboxylic acid anhydrides has altogether numerous advantages. It can be carried out as a one-pot synthesis, the starting materials, especially the acid chlorides and bromides of formula II, are easily accessible, and the carboxylic acid anhydrides of formula I are obtained in very good, almost quantitative yield and high purity without the formation of any troublesome or environmentally undesirable by-products: on the contrary, the by-products formed are acid chlorides or bromides of formula IV which are themselves very desirable reagents for organic synthesis and can be obtained direct in pure or easily purifiable form. An additional significant advantage of the novel process is that working up is carried out in an astonishingly simple manner: distillation suffices. The by-product of formula IV that forms during the reaction is always removed by distillation, preferably continuously in the course of the reaction.

In the description of this invention, the qualifying term "lower" used in the definition of groups and radicals as in lower alkyl, lower alkoxy, lower alkanoyl and the like, denotes that said groups and radicals, unless otherwise expressly stated, contain up to 7, and preferably up to 4, carbon atoms inclusive.

The general terms and expressions used in the description of this invention preferably have the following meanings:

An aliphatic radical $R_1$ typically contains up to 20 carbon atoms and is saturated or partially unsaturated.

A preferred aliphatic radical $R_1$ is unsubstituted and contains in that case not fewer than 2 to 20 carbon atoms and is in particular a saturated aliphatic hydrocarbon radical, preferably alkyl which is straight-chain or mono- or polybranched, excluding methyl, and is more particularly $C_2-C_7$alkyl, typically ethyl, n-propyl, isopropyl, butyl, isobutyl, sec-butyl, tert-butyl, pentyl, isopentyl, sec-pentyl, neopentyl, hexyl or heptyl, tert-butyl being especially preferred, and also octyl, nonyl or decyl, or an unsaturated hydrocarbon radical, preferably alkenyl, more particularly lower alkenyl, typically straight-chain or branched $C_2-C_7$alkenyl such as vinyl, propenyl, typically allyl, isopropenyl, crotyl, buten-1-yl or 2-methylpropen-2-yl, or alkynyl, typically $C_3-C_7$alkynyl such as propargyl. Most preferably $R_1$ is tert-butyl.

A preferred saturated aliphatic radical $R_1$ is also substituted straight-chain or mono- or polybranched $C_1-C_{20}$alkyl, preferably subtituted lower alkyl such as methyl, ethyl, n-propyl or isopropyl, butyl, isobutyl, sec-butyl, tert-butyl, pentyl, isopentyl, sec-pentyl, neopentyl, hexyl or heptyl, or also substituted octyl, nonyl or decyl. Preferred substituents are one or more than one, preferably up to three, typically one, of the members selected from the group consisting of lower alkoxy such as methoxy, lower alkanoyloxy such as acetoxy, phenoxy, lower alkylmercapto such as methylmercapto, lower alkoxycarbonyl such as methoxycarbonyl or tert-butoxycarbonyl, halogen, typically fluoro, chloro, bromo or iodo, oxo and/or nitro. Preferred substituents are also those functional groups that must be present in protected form during the reaction, including hydroxy, mercapto, amino, lower alkylamino such as methylamino, or carboxy. Particularly preferred substituents are lower alkoxy such as methoxy, phenoxy, lower alkylmercapto such as methylmercapto, di-lower alkylamino such as dimethylamino, halogen, typically fluoro, chloro, bromo or iodo, oxo and/or nitro, and further substituents for which no protective groups are necessary in the novel process. Halogen-substituted lower alkyl $R_1$ is particularly preferred, typically chloromethyl or bromomethyl, with chloromethyl being most preferred.

A preferred cycloaliphatic radical $R_1$ contains 3 to 20 carbon atoms and is mono-, bi- or tricyclic, preferably $C_3$–$C_8$cycloalkyl such as cyclopropyl, cyclobutyl, or, preferably, $C_5$–$C_7$cycloalkyl such as cyclopentyl, cyclohexyl or cycloheptyl, which radicals are substituted by the substituents cited in the definition of an aliphatic radical $R_1$, or also by lower alkyl such as methyl, or they are preferably unsubstituted. Cyclohexyl is very particularly preferred.

A preferred aromatic radical $R_1$ contains up to 20, preferably up to 14, carbon atoms and is preferably selected from among phenyl, naphthyl such as 1- or 2-naphthyl, indenyl such as 2- or 4-indenyl, indanyl such as 2-indanyl, anthryl such as 1-,or 2-anthryl, phenanthryl such as 9-phenanthryl, acenaphthenyl such as 1-acenaphthenyl, or fluorenyl such as 9-fluorenyl, and is preferably phenyl or naphthyl, which radicals are substituted by the substituents cited in the definition of an aliphatic radical $R_1$, or also by alkyl, preferably by lower alkyl, lower alkoxy, halogen, trifluoromethyl and/or nitro, or they are preferably unsubstituted. Phenyl is very particularly preferred.

A preferred cycloaliphatic-aliphatic radical $R_1$ is one of the substituted or, preferably, unsubstituted radicals cited in the definition of aliphatic radicals $R_1$, preferably lower alkyl such as methyl, ethyl, propyl or butyl, which is attached to one of the substituted or, preferably, unsubstituted radicals mentioned in the definition of cycloaliphatic radicals $R_1$, preferably $C_3$–$C_8$cycloalkyl such as cyclopentyl, cyclohexyl or cycloheptyl, which cycloaliphatic radical is preferably terminally bonded to the aliphatic radical. Cyclohexylmethyl is very particularly preferred.

A preferred araliphatic radical $R_1$ is one of the substituted or, preferably, unsubstituted radicals mentioned in the definition of aliphatic radicals $R_1$, preferably lower alkyl such as methyl, ethyl, propyl or butyl, which is attached to one or more than one of the substituted or, preferably, unsubstituted radicals cited in the definition of aromatic radicals $R_1$, preferably phenyl or napthyl, the substituent of the aromatic radical being most preferably lower alkyl, lower alkoxy, halogen such as fluoro, chloro or bromo, trifluoromethyl and/or nitro, and the araliphatic radical may contain one, two or three aromatic nuclei, as in mono-, di- or triphenyl-lower alkyl, or preferably contains one aromatic nucleus terminally bonded to the aliphatic radical. Phenylmethyl is very particularly preferred.

Functional groups in protected form are those which shall not participate in the reaction, typically hydroxy, mercapto, amino, monolower alkylamino or carboxy groups. These functional groups can be protected by the suitable protective groups (conventional protective groups) conventionally used in the synthesis of peptide compounds and also of cephalosporins and penicillins, nucleic acids and sugars. These protective groups may already be present in the precursors and shall protect the functional groups against unwanted side reactions such as acylations, and also etherifications, esterifications, oxidations and the like. Characteristic of protective groups is that they are easily removable, i.e without undesirable side reactions. Only those groups are designated protective groups that do not fall under the definition of the final products of formula I.

The removal of the protective groups which do not form part of the desired final product of formula I is effected in a manner known per se, typically by solvolysis, acidolysis or reduction, or also enzymatically, in some cases stepwise or with simultaneous removal of all protective groups to be removed.

The protection of functional groups by such protective groups, the protective groups themselves and the reactions to remove them are described, inter alia, in standard works, as in J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Volume 3 (ed. E. Gross and J. Meienhofer), Academic Press, London and New York 1981, in "Methoden der organischen Chemie" (Methods of Organic Chemistry), Houben Weyl, 4th Edition, Vol. 15/I, Georg Thieme Verlag, Stuttgart 1974, in H.-D. Jakubke and H. Jescheit, "Aminosäuren, Peptide, Proteine" (Amino acids, Peptides, Proteins), Verlag Chemie, Weinheim, Deerfield Beech and Basel 1982, and in Jochen Lehmann, "Chemie der Kohlenhydrate: Monosaccharide und Derivate" (The Chemistry of Hydrocarbons: Monosaccharides and Derivatives), Georg Thieme Verlag, Stuttgart 1974.

A hydroxy group is protected typically by a halogen-substituted, e.g. a chlorine-substituted, lower alkanoyl group, for example 2,2-dichloroacetyl, by 2-chloroethoxycarbonyl, 2,2,2-trichloroethoxycarbonyl, 4-nitrobenzyloxycarbonyl or diphenylmethoxycarbonyl, by tri-lower alkylsilyl, e.g. trimethylsilyl or, preferably, tert-butyldimethylsilyl, a readily removable alkyl group such as tert-lower alkyl, typically tert-butyl, an oxa- or a thiaaliphatic or thiacycloaliphatic hydrocarbon radical, e.g. 1-lower alkoxy-lower alkyl or 1-lower alkylthio-lower alkyl, e.g. methoxymethyl, 1-methoxyethyl, 1-ethoxyethyl, methylthiomethyl, 1-methylthioethyl or 1-ethylthioethyl, or 2-oxa- or 2-thiacycloalkyl containing 5–7 ring atoms, e.g. 2-tetrahydrofuryl or 2-tetrahydropyranyl, a corresponding thia analog, or by 1-phenyl-lower alkyl, e.g. benzyl, diphenylmethyl or trityl, wherein the phenyl moieties may be substituted by halogen, e.g. chloro, lower alkoxy, e.g. methoxy, and/or nitro.

A mercapto group may be protected by a benzyl radical which is substituted in the phenyl nucleus by e.g. methoxy or nitro, for example 4-methoxybenzyl, a diphenylethyl radical which is substituted in the phenyl nucleus by e.g. methoxy, typically di(4-methoxyphenyl)methyl, triphenylmethyl, by pyridyldiphenylmethyl, trimethylsilyl, benzylthiomethyl, tetrahydropyranyl, acylaminomethyl, e.g. acetamidomethyl, isobutyrylacetamidomethyl or 2-chloroacetamidomethyl, benzoyl, benzyloxycarbonyl or alkylcarbamoyl, preferably lower alkylcarbamoyl, e.g. ethylcarbamoyl, as well as lower alkylthio, e.g. S-ethylthio or S-tert-butylthio, or S-sulfo.

An amino or monolower alkylamino group may be protected by lower alkanoyl, e.g. formyl, acetyl, propionyl or pivaloyl, halo-lower alkanoyl, e.g. 2-haloacetyl, typically 2-chloroacetyl, 2-bromoacetyl, 2-iodoacetyl, 2,2,2-trifluoroacetyl or 2,2,2-trichloroacetyl, benzoyl or benzoyl which is substituted by halogen, lower alkoxy or nitro, e.g. benzoyl, 4-chlorobenzoyl, 4-methoxybenzoyl or 4-nitrobenzoyl, or lower alkoxycarbonyl which is branched in 1-position of the lower alkyl moiety or suitably substituted in 1- or 2-position, e.g. tert-lower alkoxycarbonyl such as tert-butoxycarbonyl, arylmethoxycarbonyl containing one or two aryl radicals, wherein aryl is phenyl which is unsubstituted or monoor polysubstituted by lower alkyl, tert-lower alkyl such as tert-butyl, lower alkoxy such as methoxy, hydroxy, halogen, e.g. chloro, and/or nitro, e.g. benzyloxycarbonyl, 4-nitrobenzyloxycarbonyl, diphenylmethoxycarbonyl, di(4-methoxyphenyl)methoxycarbonyl or 9-fluorenylmethoxycarbonyl, aroylmethoxycarbonyl, e.g. phenacyloxycarbonyl, 2-halo-lower alkoxycarbonyl, e.g. 2-chloroethoxycarbonyl, 2,2,2-trichloroethoxycarbonyl, 2-bromoethoxycarbonyl or 2-iodoethoxycarbonyl, 2-tri-lower alkylsilyl-lower alkoxycarbonyl, e.g. 2-trimethlysilylethoxycarbonyl, or 2-triaryisilyl-lower alkoxycarbonyl, e.g. 2-triphenylsilylethoxycarbonyl.

A carboxy group may be protected by esterification with a lower alkyl group which is branched in 1-position of the lower alkyl group, as in tert-lower alkoxycarbonyl, e.g. tert-butoxycarbonyl, or in arylmethoxycarbonyl containing one or two aryl groups wherein aryl is unsubstituted phenyl or phenyl which is mono-, di- oder trisubstituted by lower alkyl, e.g. tert-lower alkyl such as tert-butyl, lower alkoxy, e.g. methoxy, hydroxy, halogen, e.g. chloro, and/or nitro, for example benzyloxycarbonyl, benzyloxycarbonyl which is substituted by the cited substituents, e.g. 4-nitrobenzyloxycarbonyl or 4-methoxybenzyloxycarbonyl, diphenylmethoxycarbonyl or diphenylmethoxycarbonyl which is substituted by the cited substituents, e.g. di(4-methoxyphenyl)methoxycarbonyl.

A preferred aliphatic hydrocarbon radical $R_2$ is methyl or an unsaturated or, preferably, a saturated hydrocarbon radical as defined above in respect of unsubstituted aliphatic radicals $R_1$. More particularly $R_2$ is lower alkyl, typically methyl, ethyl, n-propyl, isopropyl, n-butyl, sec-butyl or tert-butyl. $R_2$ is most preferably methyl.

$R_2$ as cycloalkyl is preferably $C_3-C_6$cycloalkyl such as cyclopropyl, cyclobutyl or, most preferably, cyclopentyl or cyclohexyl.

As necessarily follows from the condition that the compounds of formula IV are removed from the reaction mixture by distillation, the following must always be taken into account in the definition of $R_1$ and $R_2$: the substituents $R_1$ and $R_2$ must be so chosen that the boiling point of the compound of formula I, and preferably also of the compounds of formulae II and III and any intermediates in the reaction mixture, is sufficiently higher than the boiling point of the compounds of formula IV to permit the compounds of formula IV to be distilled off during the reaction. Preferably the compounds of formula IV have under the reaction conditions a boiling point which is at least 10° C. lower than that of the compounds of formula II.

The compounds of formula I are useful intermediates in organic synthesis and are frequently used as substitute chemicals for the acid chlorides or bromides of formula II, as they have a somewhat lower, but still comparable, reactivity and a higher selectivity than the compounds of formula II. Thus the acid anhydrides of formula I, when used on an industrial scale, do not cause the corrosion that occurs when using acid chlorides. It is also possible to use the carboxylic acid anhydrides as intermediates for synthesising plant protection agents. For example, the acid anhydrides of formula I can be used as starting materials for the preparation of acyl cyanides (q.v. inter alia DE-OS 26 14 240, DE-OS 26 14 241, DE-OS 26 42 140, DE-OS 26 42 199), which themselves can be used as intermediates for the synthesis of 1,2,4-triazin-5-ones, compounds having outstanding herbicidal properties (q.v. DE-OS 27 33 180, DE-OS 30 03 541, DE-OS 30 08 921, DE-OS 30 02 203, DE-OS 30 09 043).

Thus, for example, benzoic anhydride can be converted by a known process into the herbicide 3-methyl-4-amino-6-phenyl-1,2,4-triazin-5-on (generic name: Metamitron) by converting, in a first step, benzoic anhydride into benzoyl cyanide by reaction with an alkali metal cyanide or anhydrous hydrocyanic acid, reacting the benzoyl cyanide so obtained in a second step, in the presence of concentrated hydrochloric acid, with ethanol and reacting in a third step the ethyl phenylglyoxalate so obtained with acetyl hydrazine to form 1-phenylglyoxalic acid ethyl ester 2-acetylhydrazone which, in a fourth step, is converted in the presence of pyridine into the above final product (q.v. inter alia DE-OS 22 24 161, DE-OS 26 14 240, DE-OS 26 14 241).

Pivalic anhydride can be convened also by known methods into the herbicide 3-methylthio-4-amino-6-tert-butyl-1,2,4-triazin-5-one (generic name: Metribuzin) (q.v. interalia DE-OS 26 14 240 and DE-OS 26 14 241 in conjunction with DE-OS 30 09 043).

The invention relates primarily to the preparation of compounds of formula I, wherein $R_1$ is $C_2-C_7$alkyl, lower alkoxy- or halogen-substituted lower alkyl, $C_2-C_7$alkenyl, $C_3-C_7$alkynyl, $C_3-C_8$cycloalkyl, unsubstituted phenyl or naphthyl or phenyl or naphthyl which are substituted by lower alkyl, lower alkoxy, halogen, trifluoromethyl and/or nitro, or triphenyl-lower alkyl which is unsubstituted or mono-, di- or trisubstituted in the phenyl nucleus by lower alkyl, lower alkoxy, halogen, trifluoromethyl and/or nitro.

The invention relates in particular to the preparation of compounds of formula I, wherein $R_1$ is $C_2-C_7$alkyl or halogen-substituted lower alkyl, such as tert-butyl or chloromethyl, $C_5-C_7$cycloalkyl, phenyl or naphthyl.

The invention preferably relates to the preparation of compounds of formula I, wherein $R_1$ is $C_2-C_7$alkyl, lower alkyl which is mono- to trisubstituted by fluoro, chloro or bromo, or phenyl.

The invention relates most preferably to the preparation of compounds of formula I, wherein $R_1$ is tert-butyl, chloromethyl or phenyl.

$R_1$ in the starting compounds of formula II in each case corresponds to the above definitions.

In the acid anhydrides of formula II $R_2$ is preferably lower alkyl or $C_3-C_6$cycloalkyl.

$R_2$ is most preferably lower alkyl.

The compound of formula II is most preferably acetic anhydride ($R_2$=methyl).

$R_2$ in the starting compounds of formula IV in each case corresponds to the above definitions.

The reaction of a compound of formula II with an acid anhydride of formula III is preferably carried out using an at least two-fold molar amount of a compound of formula II relative to the acid anhydride of formula III, in the presence or absence of a solvent or diluent, conveniently at elevated temperature and under conditions which permit the removal of the compound of formula IV by distillation, under a suitable pressure and in the absence or presence of an inert gas, as well as with subsequent optional and additional working up.

An at least two-fold molar amount of a compound of formula II relative to an acid anhydride of formula III means in particular that the molar ratio of the compound of formula II to the compound of formula III is from 2 to 10, preferably from 2 to 5, typically from 2 to 3, the limiting values being included.

Solvents or diluents are preferably aprotic inert solvents having boiling points sufficiently higher than the boiling point of the respective compound of formula IV to ensure that said compound can be continually removed by distillation during the reaction. Preferably the boiling point of the solvent or diluent is at least 100° C. higher. Also possible are those solvents which have a lower boiling point than the compounds of formula IV, so that the solvent can also be used as entrainer for the distillation of the compound of formula IV, in which case, if necessary, the reaction can be discontinued so as to replenish the solvent. Those solvents are especially preferred which have a higher boiling point than the compound of formula IV to be removed by distillation, preferably at least 10° C. higher, but at the same time have a lower boiling temperature than the products of formula I so that the solvent can be removed from the reactor by distillation after the reaction, preferably at least 10° C. lower. The solvents from which a choice may be made include in particular hydrocarbons, e.g. alkanes, typically alkanes such as hexane, pentane, heptane or octane, haloalkanes such as di-, tri- or tetrachloro-$C_1$-$C_4$alkanes, e.g. methylene chloride or trichloroethane, aromatic hydrocarbons such as benzene or toluene, halogenated aromatic hydrocarbons such as chlorobenzene, or ethers such as dioxane. However, the reaction can with advantage be carried out without a solvent, conveniently in a melt or, in particular, whenever at least the acid anhydride of formula III is liquid at the given reaction temperature so that it acts simultaneously as reagent and solvent. A particularly suitable compound of formula III is acetic anhydride.

The reaction temperature is in the range from 10° C. to the boiling temperature of the reaction mixture, and the highest permissible reaction temperature must be so chosen that no unwanted side reactions can occur. Preferably the temperature is in the range from room temperature to a maximum temperature of 200° C., i.e. from 60° to 180° C., in particular from 100° to 120° C.

The by-product of formula IV which forms during the reaction is removed by distillation, preferably continuously in the course of the reaction.

To meet the condition of ensuring the removal of the compound of formula IV by distillation, the limitations cited above in the definition of further solvents and diluents will apply if such solvents or diluents are present. In the preferred mode of carrying out the reaction with a solvent, the prerequisite is, as mentioned above in the definition of $R_1$ and $R_2$, that these radicals must be so chosen that the boiling point of the compound of formula I, preferably also that of the compounds of formulae II and III, is always sufficiently higher than the boiling point of the compounds of formula IV to ensure the removal by distillation of the compounds of formula IV in the course of the reaction. The compound of formula IV preferably has a boiling point which, under the given reaction conditions, is at least 10° C. lower than that of the compound of formula II. A particularly preferred compound of formula II is therefore acetic anhydride.

Suitable pressures for carrying out the reaction are preferably atmospheric pressure or, especially in the case of reaction mixtures whose boiling point is higher than the value cited above according to the definition of the highest permissible temperature, reduced pressures, preferably of 1 mbar to atmospheric pressure, conveniently 10 to 900 mbar or atmospheric pressure, preferably 100 to 600 mbar or atmospheric pressure, typically about 400 mbar or atmospheric pressure.

The reaction can be carried out with or, preferably, without an inert gas such as nitrogen or argon, especially nitrogen.

The subsequent further working up is carried out preferably by removing excess solvent and diluent by distillation and, if there is an excess of the compound of formula II, by removing said excess, preferably by distillation. Distillation is carried out under atmospheric pressure or reduced pressure, depending on the boiling point of the starting compound of formula II, preferably under reduced pressure, conveniently at 1 to 1000 mbar, preferably at 5 to 500 mbar, as from 2 to 200 mbar, typically at about 5 to 10 or at about 150 mbar. Furthermore, protected functional groups, as described above, can be deprotected.

The end of the reaction can be determined by standard analytical methods, for example gas chromatography, or simply by measuring the boiling temperature of the reaction mixture determined by such analytical methods and at which the entire by-product of formula IV is distilled off.

The invention more preferably relates to the process which comprises reacting chloroacetyl chloride of formula II and acetic anhydride of formula III in the molar ratio of 2:1 to 5:1 at 100° to 120° C., with simultaneous removal by distillation of the resultant acetyl chloride of formula IV, to form the chloracetic anhydride of formula I which, after distillation of excess chloroacetyl chloride under reduced pressure of 2 to 200 mbar, is obtained in pure form.

The invention also very preferably relates to the process which comprises reacting benzoyl chloride of formula II and acetic anhydride of formula III in the molar ratio of 2:1 to 5:1 at 100° to 120° C., with simultaneous removal by distillation of the resultant acetyl chloride of formula IV, at 100 to 600 mbar to form the benzoic anhydride of formula I which, after distillation of excess benzoyl chloride of formula IV under reduced pressure of 2 to 200 mbar, is obtained in pure form.

Finally, the invention also relates most preferably to the process which comprises reacting pivaloyl chloride of formula II and acetic anhydride of formula III in the molar ratio of 2:1 to 5:1 at 100° to 120° C., with simultaneous removal by distillation of the resultant acetyl chloride of formula IV, to form the pivaloyl anhydride of formula I which, after distillation of excess pivaloyl chloride of formula IV under reduced pressure of 2 to 200 mbar, is obtained in pure form.

The invention relates first and foremost to the preparation described in the Examples of the compounds of formula I mentioned therein, specifically chloroacetic anhydride ($R_1$=chloromethyl), benzoic anhydride ($R_1$=phenyl) and pivalic anhydride ($R_1$=tert-butyl).

Starting compounds

In the compounds of formula II and their precursors, any groups present in $R_1$ may, if necessary, be in protected form. The introduction and the removal of protective groups are effected as described in the definition of protective groups.

The starting compounds of formula II are known, are prepared by the standard methods of obtaining carboxylic acid chlorides and bromides, or they are commercially obtainable.

For example, the free carboxylic acids can be converted into the corresponding carboxylic acid chlorides by reaction with inorganic acid chlorides such as phosphoroxy chloride, phosphorus trichloride and thionyl chloride. The reaction of the free carboxylic acids with oxalyl chloride is also suitable for converting sensitive carboxylic acids into their halides. The acid bromides of formula II can be conveniently obtained with analagous inorganic acid bromides or from the acid chlorides by treatment with dry hydrogen bromide.

The carboxylic acid anhydrides of formula III are likewise known, are obtainable by known methods or are commercially available.

For example, they can be prepared by one of the methods described in Houben-Weyl, "Methoden der Organischen Chemie" (Methods of Organic Chemistry), Supplementary Volume and Sequel to the 4th Edition Vol. E5 "Carbonsäuren und Carbonäure-Derivate" (Carboxylic acids and Derivatives), Stuttgart/New York 1985, pp. 633 to 652.

The invention is illustrated by, but not limited in scope to, the following Examples. Temperatures are indicated in degrees Celsius (°C.) and pressures are given in mbar.

Example 1: Chloroacetic anhydride 613 g of acetic anhydride (6 mol) are mixed with 2000 g of chloroacetyl chloride (17.7 mol) and the mixture is heated to 100°-120° C. The resulting acetyl chloride is removed by distillation. Upon termination of the reaction, excess chloroacetyl chloride is removed by distillation under reduced pressure (about 150 mbar). The residue consists of pure chloroacetic anhydride. Yield: 1016 g (=99% of theory) of chloroacetic anhydride.

Example 2: Benzoic anhydride 300 g of benzoyl chloride (2.13 mol) are mixed with 91 g of acetic anhydride (0.89 mol) and the mixture is heated to 100° to 120° C. The resultant acetyl chloride is removed by distillation under reduced pressure (400 mbar) and, upon completion of the reaction, excess benzoyl chloride is removed by distillation at about 7 mbar. The residue consists of pure benzoic anhydride. Yield: 200 g (=99% of theory) of benzoic anhydride.

Example 3: Pivalic anhydride 400 g of acetic anhydride (3.92 mol) are mixed with 1200 g of pivaloyl chloride (9.95 mol) and the mixture is heated to 100°-120° C. The resultant acetyl chloride is removed by distillation. Upon termination of the reaction, excess pivaloyl chloride is removed by distillation under a reduced pressure of about 150 mbar. The residue consists of pure pivalic anhydride. Yield: 722 g (=99% of theory) of pivalic anhydride.

What is claimed is:

1. A process for the preparation of a symmetrical acid anhydride of formula

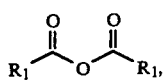

wherein $R_1$ is an aliphatic, cycloaliphatic, aromatic, cycloaliphatic-aliphatic or araliphatic radical, with the proviso that functional groups present in $R_1$, if necessary, are in protected form, which process comprises reacting a compound of formula

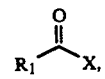

wherein $R_1$ has the meanings assigned to it above, and wherein X is chloro or bromo, with an acid anhydride of formula

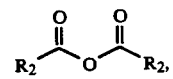

wherein $R_2$ is an aliphatic hydrocarbon radical or cycloalkyl, with removal by distillation of the compound of formula

wherein $R_2$ and X have the meanings assigned to them above, and removing any protective groups present.

2. A process according to claim 1 which comprises the use of compounds of formulae II and III, wherein $R_1$ is $C_2$-$C_7$alkyl, lower alkoxy- or halogen-substituted lower alkyl, $C_2$-$C_7$alkenyl, $C_3$-$C_7$alkynyl, $C_3$-$C_8$cycloalkyl, unsubstituted phenyl or naphthyl or phenyl or naphthyl which are substituted by lower alkyl, lower alkoxy, halogen, trifluoromethyl and/or nitro, or triphenyl-lower alkyl which is unsubstituted or mono-, di- or trisubstituted in the phenyl nucleus by lower alkyl, lower alkoxy, halogen, trifluoromethyl and/or nitro.

3. A process according to claim 1 which comprises the use of compounds of formulae I and II, wherein $R_1$ is $C_2$-$C_7$alkyl, halogen-substituted lower alkyl, $C_5$-$C_7$cycloalkyl, phenyl or naphthyl.

4. A process according to claim 1, wherein the reaction temperature is in the range from room temperature to the boiling point of the reaction mixture, but does not exceed 200° C.

5. A process according to claim 3, wherein the reaction temperature is in the range from room temperature to the boiling point of the reaction mixture, but does not exceed 200° C.

6. A process according to claim 1, wherein the molar ratio of the compound of formula H to the anhydride of formula III is from 2 to 10.

7. A process according to claim 3, wherein the molar ratio of the compound of formula II to the anhydride of formula III is from 2 to 10.

8. A process according to claim 1, wherein the compound of formula IV is removed by distillation under atmospheric pressure or under reduced pressure.

9. A process according to claim 3, wherein the compound of formula IV is removed by distillation under atmospheric pressure or under reduced pressure.

10. A process according to claim 1, wherein the substituents $R_2$ in acid anhydrides of formula III are so chosen that the boiling point of the compound of formula IV is more than 10° C. below that of the compound of formula II, but does not exceed 200° C.

11. A process according to claim 3, wherein the substituents $R_2$ in acid anhydrides of formula III are so chosen that the boiling point of the compound of formula IV is more than 10° C. below that of the compound of formula II, but does not exceed 200° C.

12. A process according to claim 1, which comprises separating a mixture of compounds of formulae I and II by distillation after the reaction if an excess of compound of formula II relative to the acid anhydride of formula III is present.

13. A process according to claim 3, which comprises separating a mixture of compounds of formulae I and II by distillation after the reaction if an excess of compound of formula II relative to the acid anhydride of formula III is present.

14. A process according to claim 1, wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

15. A process according to claim 2, wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

16. A process according to claim 3, wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

17. A process according to claim 9, which comprises the use of compounds of formula II and III, wherein $R_1$ is $C_2$-$C_7$alkyl, lower alkyl which is mono- to trisubstituted by fluoro, chloro or bromo, or phenyl, and $R_2$ is lower alkyl, in the compounds of formulae II and IV X being chloro, and wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

18. A process according to claim 1, which comprises the use of compounds of formula II and III, wherein $R_1$ is tert-butyl, chloromethyl or phenyl, and $R_2$ is methyl, in the compounds of formulae II and IV X being chloro, and wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

19. A process according to claim 1, which comprises the use of compounds of formula II and III, wherein $R_1$ is tert-butyl and $R_2$ is methyl, in the compounds of formulae II and IV X being chloro, and wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

20. A process according to claim 1, which comprises the use of compounds of formula II and III, wherein $R_1$ is chloromethyl and $R_2$ is methyl, in the compounds of formulae II and IV X being chloro, and wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

21. A process according to claim 1, which comprises the use of compounds of formula II and III, and wherein $R_1$ is phenyl and $R_2$ is methyl, in the compounds of formulae II and IV X being chloro, wherein the reaction temperature is in the range from room temperature to the boiling point of the reaction mixture, but does not exceed 200° C., the molar ratio of the compound of formula II to the anhydride of formula III is from 2 to 10, the compound of formula IV is removed by distillation under atmospheric pressure or under reduced pressure, and the substituents $R_2$ in acid anhydrides of formula III are so chosen that the boiling point of the compound of formula IV is more than 10° C. below that of the compound of formula II, but does not exceed 200° C.

22. A process according to claim 1, which comprises reacting chloroacetyl chloride of formula II and acetic anhydride of formula III in the molar ratio of 2:1 to 5:1 at 100 to 120° C., with simultaneous removal by distillation of the resultant acetyl chloride of formula IV, to form the chloracetic anhydride of formula I which, after distillation of excess chloroacetyl chloride under reduced pressure of 2 to 200 mbar, is obtained in pure form.

23. A process according to claim 1, which comprises reacting benzoyl chloride of formula II and acetic anhydride of formula III in the molar ratio of 2:1 to 5:1 at 100 to 120° C., with simultaneous removal by distillation of the resultant acetyl chloride of formula IV at 100 to 600 mbar, to form the benzoic anhydride of formula I which, after distillation of excess benzoyl chloride of formula IV under reduced pressure of 2 to 200 mbar, is obtained in pure form.

24. A process according to claim 1, which comprises reacting pivaloyl chloride of formula II and acetic anhydride of formula III in the molar ratio of 2:1 to 5 : I at 100 to 120° C., with simultaneous removal by distillation of the resultant acetyl chloride of formula IV, to form the pivaloyl anhydride of formula I which, after distillation of excess pivaloyl chloride of formula IV under reduced pressure of 2 to 200 mbar, is obtained in pure form.

* * * * *